United States Patent [19]

Dahms

[11] 4,005,983
[45] Feb. 1, 1977

[54] METHOD AND APPARATUS FOR COLORIMETRIC ANALYSIS

[76] Inventor: Harald Dahms, 22 Lakeview Road, Ossining, N.Y. 10562

[22] Filed: June 21, 1974

[21] Appl. No.: 481,803

Related U.S. Application Data

[60] Division of Ser. No. 297,597, Oct. 16, 1972, abandoned, which is a continuation of Ser. No. 89,228, Nov. 13, 1970, abandoned.

[52] U.S. Cl. .............................. 23/230 R
[51] Int. Cl.² .................. G01N 31/22; G01N 33/18
[58] Field of Search .................. 23/230 R, 230 HC; 252/408

[56] References Cited

UNITED STATES PATENTS 2,395,489  2/1946  Major et al. ................. 23/232 R
3,476,516  11/1969  Curry ........................ 23/254 R

OTHER PUBLICATIONS

Mitchell et al., Aquametry, Interscience Publ., New York, 1948, pp. 23, 168, 171, 172.
Mitchell et al., Anal. Chem., 22, 484 (1950).

Primary Examiner—Robert M. Reese

[57] ABSTRACT

A colorimetric test for water in a vial which is prepacked with Karl-Fischer-Reagent and a colorimeter for direct readout of water content.

7 Claims, 10 Drawing Figures

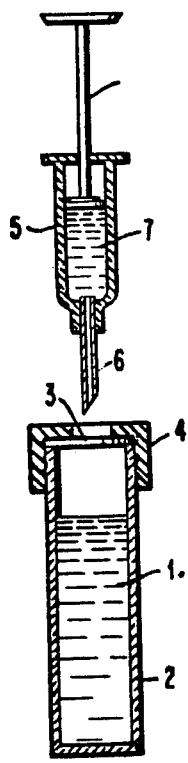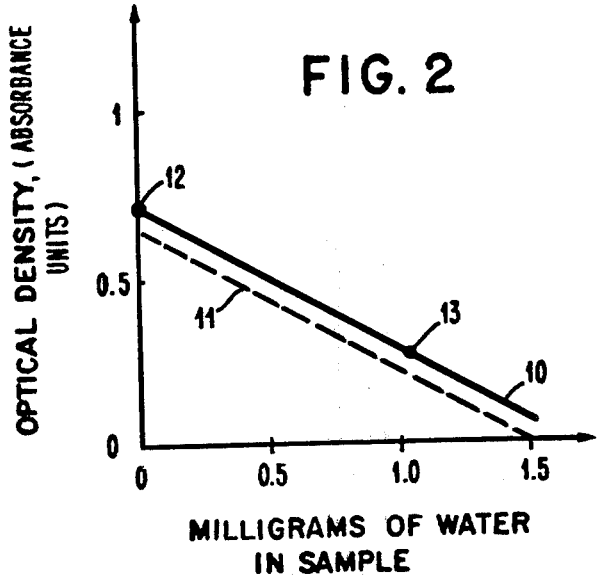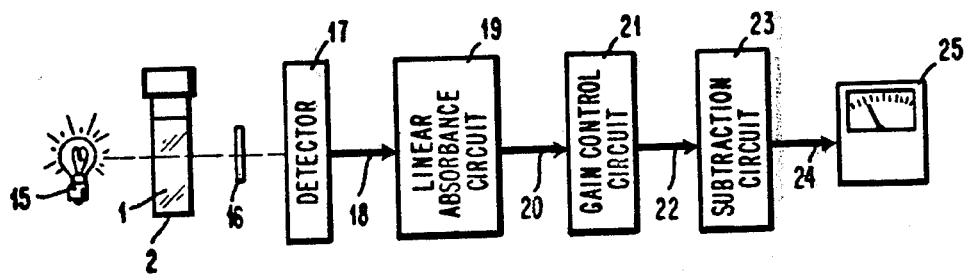
FIG. 1
FIG. 2
FIG. 3

METHOD AND APPARATUS FOR COLORIMETRIC ANALYSIS

This is a division of application Ser. No. 297,597, filed Oct. 16, 1972, which is a continuation of Ser. No. 89,228, filed Nov. 13, 1970, both now abandoned.

BACKGROUND OF THE INVENTION

1. Field of the Invention

This invention relates to analytical determinations by colorimetric means, in particular to the determination of water.

2. DESCRIPTION OF THE PRIOR ART

The determination of the water content is important for many commercial products. For example, minute quantities of water in chemical process streams are detrimental for certain reactions. The electrical properties of insulators are strongly dependent on water traces. The water content of gasoline has to be kept below a certain level. The moisture of tobacco products has to be closely controlled. These few examples show that water determinations are among the most frequently performed analyses in many laboratories.

The currently most widely practiced method of water determination is the "Karl Fischer Method", named after its orginator Karl Fischer who described the basis of the method in "Zeitschrift fuer Angewandte Chemie", Volume 48, pages 394–396 in 1935. In this method the sample containing an unknown amount of water is titrated with "Karl-Fischer-Reagent", hereinafter also called NF Reagent. This reagent is usually a solution of iodine and sulfur dioxide in pyridine and methanol or other solvents. It is believed that these species react with water according to

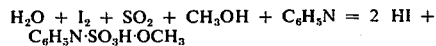

$$H_2O + I_2 + SO_2 + CH_3OH + C_5H_5N = 2\ HI + C_5H_5N\cdot SO_3H\cdot OCH_3$$

The KF reagent is dark brown, the color being mainly attributed to the presence of iodine. In the reaction with water the iodine is consumed so that the dark brown color of the iodine in the "fresh" reagent disappears, changing to a light yellow color of the "spent" reagent.

In a typical water determination by the Karl-Fischer-Method the endpoint of the titration is detected visually by the color change from dark brown to light yellow or by other means such as electrical signals. These electrical endpoint detection means are, however, outside the scope of this invention.

There are several disadvantages in the present Karl-Fischer Methods. Among the most serious drawbacks is the fact that the strength of the KF reagent decreases with age, i.e. the iodine content of the reagent decreases with time even when moisture is absolutely excluded from the reagent. Since its strength is unknown the KF reagent has to be calibrated with a sample of known water content before an actual water determination can be run. Another disadvantage is the fact that moisture of the atmosphere has to be meticulously excluded from the titration. The KF reagent is so sensitive that any contact of reagent with the atmosphere (which contains moisture) leads to incorrect results. Titration vessels have to be dried and flushed with dry gases, and the titration assembly has to be protected from moisture. These elaborate preparations, combined with the necessary calibration of the reagent, amount to a considerable preparation time for each determination.

In the practice of the present invention the water-containing sample is injected into a prepacked volume of KF reagent and the change in optical absorbance of the KF reagent is measured. The change in optical absorbance is transformed by an electric circuit into a direct readout of the water content of the sample. This method gives immediately quantitative results, irrespective of the fading of strength of the reagent during storage.

It is, therefore, an object of the present invention to provide apparatus and methods for fast and simple determinations of the water content of samples.

The foregoing and other objects, features, and advantages of the invention will be apparent from the following more particular description of the preferred embodiments of the invention.

In the drawings:

FIG. 1 is a cross-sectional view of the colorimetric tube and of the injection syringe.

FIG. 2 is a plot of data showing the dependence of the optical absorption of the KF reagent on the water content of the sample.

FIG. 3 is a schematic block diagram of the apparatus for indicating directly the water content of the sample.

Figure 5:
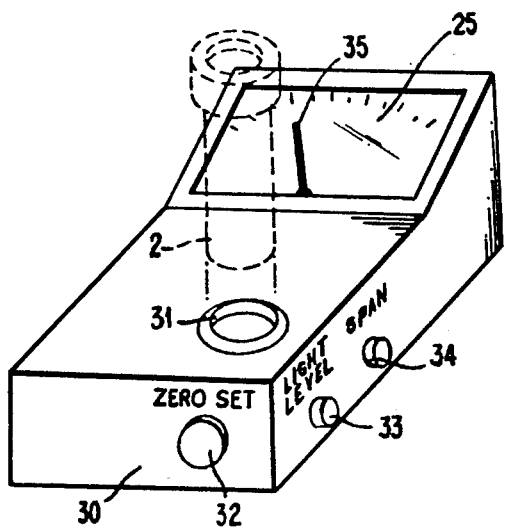
FIG. 5 shows a view of the apparatus for direct readout of water content.
Figure 6:
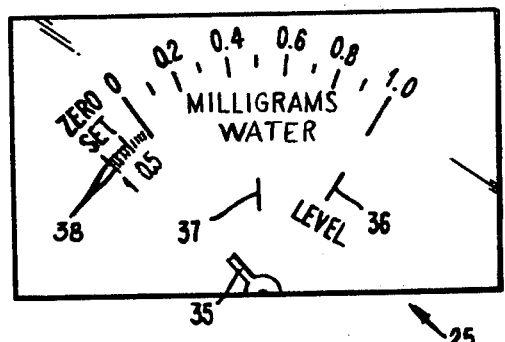
Figure 7:
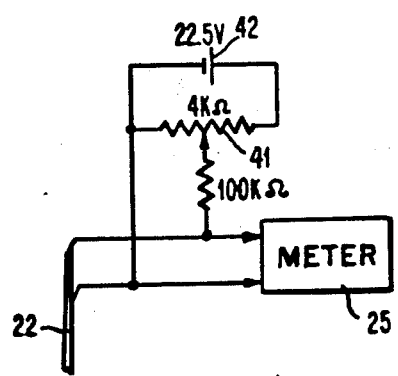

FIG. 6 gives a detailed view of the meter scale used in the apparatus shown in FIG. 5. FIG. 7 is a diagram of an electric circuit which performs the subtraction function in the apparatus.

DETAILED DESCRIPTION OF THE PREFERRED EMBODIMENTS

Referring now to FIG. 1 there is shown a glass vessel 2 containing a certain volume of the KF reagent 1. The glass vessel is covered with liner 3 which is held by screw cap 4. Liner 3 is made of a material which does not react with KF reagent and which is not permeable by water. Teflon of one tenth of an inch thickness is, for example, such material. A known volume of the sample to be analyzed, 7, is contained in syringe 5. The sample is injected by piercing liner 3 with needle 6 and pushing piston 8 downward. The sample is then distributed throughout the KF reagent by shaking or inverting vessel 2. Since the hole pierced into liner 3 is only of the order of one sixteenth of an inch or less in diameter, there will be neither appreciable loss of reagent nor entrance of moisture into the vessel. An alternate procedure is to unscrew cap 4 and to introduce the sample without piercing liner 3. Cap 4 is then screwed back on, and the solutions are mixed by inverting vessel 2.

Vessel 2 is of the type suitable for colorimetric analysis. For example, round glass vessels of uniform wall thickness, as commonly used in colorimetry, are suitable. Rectangular optical cells may, of course, also be used.

FIG. 2 shows the optical density of the filled vessel 2 in dependence of the water content of sample 7, indicated by line 10. I measured this dependence experimentally as specified below. With identical measurements after storing the reagent for 1 week, I obtained line 11. The lowering of the curve is due to the decreasing strength of the KF reagent which has been mentioned above, being a well known fact to workers in the field. I have also observed that the strength of the KF reagent increased slightly with age in some instances. Both, increase and decrease of strength with time will not affect the analytical results since they are corrected by means of the electric circuit which is described below.

Figure 4A:
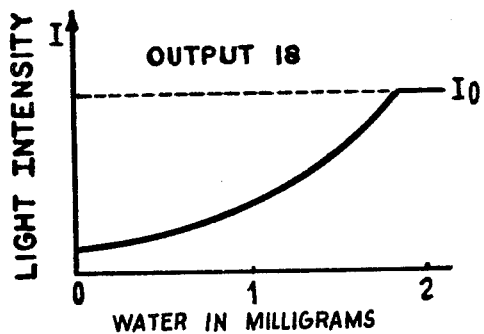
FIGS. 4A–4D show diagrams of the electric signals in dependence of water content of the sample at various stages of the electric circuit.

Direct readout of water content is obtained in the apparatus shown schematically in FIG. 3. Light from a light source 15 is passing through vessel 2 containing KF reagent, 1. The light is partly absorbed by the reagent. "Fresh" KF reagent absorbs the most light so that the light passing through the vessel, which will be called I, is at its lowest intensity. Any addition of water will lighten the color of the reagent so that more light is allowed to pass through vessel 2. This relationship is shown in FIG. 4A. When an increasing amount of water is added to the KF reagent, all of the iodine will eventually be reacted so that the light level passing through the vessel reaches its upper limit $I_o$, as shown in FIG. 4A.

Referring back to FIG. 3, the light passing through vessel 2 has to pass through filter 16. Filter 16 passes substantially only light of a certain range of wavelengths. The wavelength of this light is selected such that it is absorbed by fresh KF reagent while light absorption by spent KF reagent is substantially less.

Figure 4B:
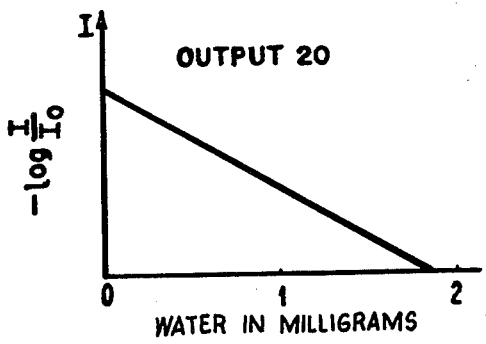

I have used, for example, a filter having a peak of transmittance at 520 nanometers with light being transmitted in the range from 500 to 550 nanometers. I have also used a filter transmitting between 590 and 630 nanometers. The filtered light is measured by light detector 17. The electric output of detector 17 is essentially proportional to the intensity of the incident light I so that the electric output 18 is also represented by the curve shown in FIG. 4A. The electric signal 18 is fed into electric circuit 19 which converts the electric signal into an electric signal resembling the function $-\log I/I_o$. Output 20 of electric circuit 19 resembles the curve shown in FIG. 4B. The quantity $-\log I/I_o$ is a well known quantity in optical measurements, the so-called "absorbance".

It is understood that the particular parts of the apparatus represented by numbers 15 to 20 are employed in commercially available instruments. A typical instrument of ths type is, for example, the "Model 44 Spectrophotometer" manufactured by Coleman Instruments, Maywood, Illinois. Other instruments delivering "linear absorbance readings" are known to those skilled in the art. Filter 16 can be substituted by gratings for the selection of certain desired wavelengths.

Figure 4C:
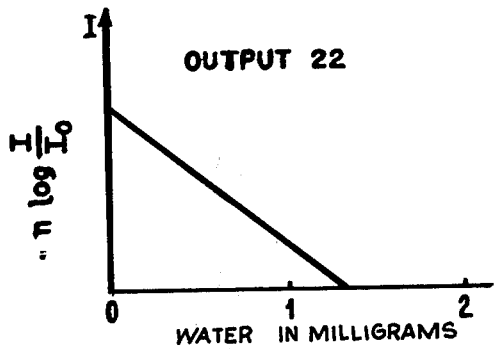
Figure 4D:
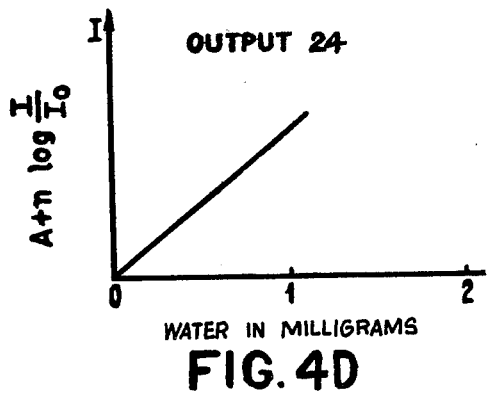

Continuing now in the description of FIG. 3, the electrical output 20 is fed into gain control circuit 21 which allows to multiply output 20 by a factor $n$. Gain control 21 permits the selection of the factor $n$. The factor $n$ determines the range of the device. Output 22 of gain control 21 is represented in FIG. 4C. Output 22 is then fed into electric circuit 23 which subtracts the input 22 (which is equal to $-n \log I/I_o$) from a constant A. The value of A is variable by a suitable control. FIG. 4D represents the output 24. Output 24 drives meter readout 25. It can be seen from FIG. 4D that the meter can be directly read in terms of water content of the sample.

It is understood that the electrical circuitry needed for performing the specified operations such as variable gain and subtraction is well known to persons skilled in the art. There is a wide variety of electrical circuitry known which performs those operations. No particular electric circuit is, therefore, specified.

While less preferable, a water determining apparatus can also operate without linear absorbance circuit 19. The loss of linearity may be corrected by spacing the marks on the motor readout 25 accordingly.

FIG. 5 shows a view of an embodiment of the instrument. The housing 30 contains the circuitry shown schematically in FIG. 3. The housing is also equipped with meter 25 and with test tube well 31 which receives prepacked test tubes of the type shown in FIG. 1. Housing 30 is also equipped with controls 32–34. Control 32 labelled "Zero set" serves to adjust the subtraction circuit 23 (FIG. 3). Control 33 labelled "Light level" serves to adjust the detector light level being measured by detector 17 (FIG. 3). Control 34 labelled "Span" serves to adjust the gain control circuit 21 (FIG. 3). A detailed view of meter scale 25 is shown in FIG. 6. The scale ranges from 0 to 1 milligrams of water. There are also zero set marks, 38, which are used for various sample sizes. If, for example, the sample size is 1 ml, the needle is adjusted at the 1 ml mark. These marks are left of the zero milligram water mark since the KF reagent is diluted when the sample is introduced. There is a decrease in optical density due to this dilution which increases with sample size. The marks on the zero set scale, 38, correct for this effect.

The instrument is typically operated in the following manner. First the light level is adjusted. For this purpose the "zero set" control 32 is turned all the way counterclockwise in which position the adjustable constant A is equal to zero. A test tube containing spend KF reagent or plain methanol is inserted into test tube well 31 and the meter needle 35 is adjusted by turning light level control 33 until it coincides with mark 36 labelled "calibration level" on meter 25 (FIG. 6). The test tube is then removed from well 31 and another test tube is inserted. This test tube contains KF reagent having a known strength, for example a strength equivalent to 0.5 milligrams of water. After insertion of this test tube into test tube well 31, Span control 34 is adjusted so that meter needle 35 points to mark 37 labelled "Span" (FIG. 6). The solution used for setting the calibration span may be a solution other than actual KF reagent, having suitable optical absorbance in the desired wavelength range. For example, a solution of iodine in pyridine and methanol may be used. The instrument is now ready for measurements. A tube containing KF reagent is inserted into test tube well 31. The meter needle 35 is then adjusted by means of "zero set" control 32 to coincide with zero milligrams water. The desired zero set point depends on the sample size. Since large samples will decrease the absorbance of the KF reagent (even if the samples do not contain any water) the zero point for larger samples is more to the left of the scale. This is indicated by the zero set scale 38 (FIG. 6).

After setting the needle to the appropriate zero mark the test tube containing the KF reagent is removed from the sample well. The sample of unknown water content is then added to the test tube. Sample and KF reagent are mixed by inverting the test tube several times. The test tube is then inserted into test tube well 31 and the water content of the sample is read on meter 25.

For measuring the water content of additional samples it is usually not necessary to repeat the whole procedure described above. The calibration of the instrument will usually remain stable for long periods, several hours or longer. It is only necessary to perform the following steps: (1) Take a new test tube prepacked with a known volume of KF reagent and insert it into test tube well 31 of the colorimeter. (2) Adjust meter needle 35 to appropriate zero set mark 38. (3) Add sample of unknown water content to the test tube and mix contents. (4) Insert test tube into well 31 and read water content on meter.

It can be seen that the procedure is extremely simple so that it can be performed with little training. It is understood that readout of the instrument is not restricted to a needle meter. Other devices such as digital readouts can be employed. It is also understood that the method is not limited to the range of 0 to 1 milligrams of water. Higher or lower ranges can be covered by changing parameters such as strength and volume of the KF reagent as well as the wavelength of the light. A decrease of volume of the KF reagent will lead to a more sensitive system since a given amount of water will lead to a large decrease in absorbance. A change in wavelength of the light will also change the sensitivity of the method. I have found, for example, that an identical KF reagent had the following absorbances at the following wavelength: An absorbance of 0.185 at 600 nanometers, 0.42 at 565 nanometers, 0.60 at 520 nanometers. The method is, therefore, not restricted to any particular wavelength.

It is further understood that the method is not restricted to measuring the water content of samples which are miscible with KF reagent. The water content of solids can be determined by adding a known amount of solids to the prepacked test tube. Also non-miscible liquids such as certain oils can be measured. The test tube containing the KF reagent and the samples of oil is skaken until all water has reacted with the KF reagent. Furthermore, gases can be introduced into the test tubes for the determination of their water content.

The strength of the KF reagent has to be chosen such that it is suitable for optical measurements. The absorbance of the test tube filled with KF reagent should usually not exceed an absorbance of 2. More preferably, the absorbance should be below 1.

It is important for the present method that the linear absorbance range extends over as much or preferably more than the water range shown on the meter. For example, if the meter range is from 0 to 1 milligrams of water, the KF reagent should be capable of reacting with more than 1 milligram of water, preferably with about 1.5 to 2 milligrams of water.

The volume of the KF reagent in each colorimetric vessel is usually between 0.5 and 50 milliliters and more preferably between 2 and 20 milliliters.

EXAMPLE

A "Diagnostest Computer Colorimeter" as sold by Diagnostics Division of Dow Chemical Corporation, Indianapolis, Indiana was operated with Filter No. 5 at a wavelength of 595 nanometers. The instrument was modified by connecting the circuit shown in FIG. 7 to the readout meter 40. This circuit acts as the subtraction unit 23, shown in FIG. 3. It is adjustable by potentiometer 41. The battery 42 delivering 22.5 V was an RCA battery VS 102. Test tubes having Teflon-lined screw caps were obtained from the A. H. Thomas Co., Philadelphia, Pa. under their catalog No. 9447–A6. These test tubes had an outer diameter of 13 millimeters. They were filled with 5 milliliters of dry methanol and 2 milliliters of KF reagent. The KF reagent consisted of 133 grams of iodine, 425 milliliters of methanol, 425 milliliters of pyridine, and 90 grams of sulfur dioxide. The absorbance of the filled test tubes was in the range of 0.6 to 0.65 as measured with the colorimeter. The potentiometer 41 was turned fully counterclockwise (no current applied to the meter). A test tube containing spent KF reagent was inserted into the colorimeter. With the selector switch in the "colorimeter" position, the control knob "colorimeter zero" was adjusted so that the meter read zero absorbance. The selector switch was then turned to the "computer" position. The "computer zero" control was then adjusted to zero. The colorimeter was then standardized by inserting a test tube with Karl Fischer solution. The strength of this KF reagent was such that its absorbance was equivalent to 0.5 milligrams of water. The meter needle was set to half scale with the calibration control (functioning as gain control 21) so that the full scale covers 1 milligram of water. The absorbance equivalent to 0.5 milligrams of water was 0.2. After the completion of the calibration a test tube with KF reagent (absorbance 0.6 to 0.65, as previously mentioned) was inserted into the colorimeter. Potentiometer 41 was adjusted such that the meter indicated full scale, the right side of the meter representing no water, and the left side of the meter scale representing 1 milligram of water. The sample containing the unknown amount of water was now added to the KF reagent. After mixing the sample and the KF reagent the water content of the sample was read on the scale. When adding samples of known water content the dependence shown as curve 10 in FIG. 2 was obtained.

I have also used the so called "stabilized karl Fischer solution" as supplied by Mallinckrodt Chemical Company in my invention. These stabilized reagents are believed to show little or no loss of strength with age so that they are well suited for my instrument. It should be understood that my invention is not restricted to any particular composition of KF reagent. Many modifications in the chemical composition of KF reagent have been described over the last 35 years which are suitable for my method. Such modifications include the concentration of iodine and iodide, the concentration of sulfur dioxide, the addition of other solvents to methanol, the replacement of methanol by other solvents etc. It is only necessary that such KF reagent decreases its optical density when water is added to be suitable for my method.

While I have described the apparatus as having optical filters as generally used in colorimeters for the selection of light of a suitable wavelength it is understood that other means of selecting certain wavelengths can be used. For example, spectrophotometers with optical gratings may be employed. The term "colorimeter" and "colorimetric means" as used in this application shall include any apparatus which provides an electric output signal which is directly proportional to light intensity of a selected wavelength range.

It is also understood that instead of the meter readout shown in FIG. 6 a digital readout can be used. Such digital readout will have provisions for zero-set and calibration equivalent to those shown in FIG. 6.

While the colorimetric apparatus has been described for the particular purpose of determining water it is understood that this colorimetric apparatus may be used for the determination of other species. The apparatus can be used whenever the species to be analyzed reacts with a reagent which absorbs light. The reaction between the species and the reagent will decrease the light absorption and this decrease may be measured with the apparatus at a suitable wavelength to determine the amount of such species. Referring to the embodiment of the colorimetric apparatus shown in FIG. 5 the procedure is as follows: In order to calibrate the apparatus, "zero set" control 32 is turned all the way counterclockwise in which position the adjustable constant A is equal to zero. Alternatively, the adjustable constant A is temporarily made equal to zero by an additional electric switch which disconnects battery 42 (FIG. 7) from the circuit during calibration. A test tube containing a blank solution is inserted into test tube well 31 and the meter needle 35 is adjusted by turning light level control 33 until it coincides with mark 36 labelled "calibration level" on meter 25 (FIG. 6). The test tube is then removed from well 31 and another test tube is inserted. This test tube contains the reagent at a known concentration which is suitable for calibration. After insertion of this test tube into test tube well 31, span control 34 is adjusted until meter needle 35 points to mark 37 labelled "Span" (FIG. 6). The instrument is now calibrated and is ready for measurements. A test tube containing the reagent solution is inserted into test tube well 31. The meter needle 35 is then adjusted by means of "zero set" control 32 to coincide with the appropriate zero level mark on the left of scale 25. A sample containing the species to be determined is now added to the test tube. Reagent and sample are mixed and reacted. With the test tube in sample well 31, the amount of species is read on meter 25. Any additional samples can now be analyzed in this way without having to repeat the calibration procedure.

It is understood that the foregoing detailed description is merely given by way of illustration and that many variations may be made therein without departing from the spirit of the invention. The "Abstract" given above is merely for the convenience of searchers and is not to be given any weight in defining the scope of the invention.

I claim:

1. A method for determining the water content of a sample, comprising the steps of:
    measuring the optical density of a known volume of first KF reagent, said KF reagent having an optical density which is substantially linearly related to the amount of water added thereto,
    adding a sample containing an unknown amount of water to said KF reagents
    measuring the optical density of said KF reagent after addition thereto of said sample containing an unknown amount of water, and
    determining the amount of water in said sample using said linear relationship between optical density and water content of said KF reagent.

2. The method of claim 1, where said sample is a liquid.

3. The method of claim 1, where said sample is a solid.

4. The method of claim 1, where said sample is a gas.

5. The method of claim 1, wherein the water content of a second sample is determined by measuring the optical density of a KF solution having the same composition as said first KF reagent, adding a sample containing an unknown amount of water to said KF solution, and calculating the amount of water in said sample using the linear relationship between optical density and water content of said first KF reagent.

6. A method for determining the amount of water in a sample, comprising the steps of:
    selecting a KF reagent whose optical density $\sigma$ is related to the amount (X) of water added to said reagent by the expression $\sigma = MX + B$ over a range of X, where the value $B$ is a constant and the slope $M$ is a constant which has been determined.
    adding said sample containing an unknown amount of water therein to said first KF reagent,
    measuring the optical density of said first KF reagent with said sample added thereto, and
    determining the amount of water in said sample using the slope M relating water content X to optical density $\sigma$ of said reagent.

7. A method for determining the strength of a KF reagent, comprising the steps of:
    selecting a KF reagent which exhibits a substantially linear relationship between its optical density and the amount of water added thereto over a range of water,
    measuring the optical density of said KF reagent, and establishing its strength, said strength being the amount of water which must be added to said KF reagent to consume the entire amount of said KF reagent, using said linear relationship established between said optical density and the amount of water added to said reagent.

* * * * *